US012782247B2

(12) United States Patent
Gerken et al.

(10) Patent No.: US 12,782,247 B2
(45) Date of Patent: Nov. 3, 2026

(54) DEVICE AND METHOD FOR EXTRACTING WATER FROM A SOIL SAMPLE

(71) Applicant: Christian-Albrechts-Universitaet zu Kiel, Kiel (DE)

(72) Inventors: Martina Gerken, Kiel (DE); Igor Titov, Borgstedt (DE); Soenke Boeckmann, Kiel (DE)

(73) Assignee: Christian-Albrechts-Universitaet zu Kiel, Kiel (DE)

( * ) Notice: Subject to any disclaimer, the term of this patent is extended or adjusted under 35 U.S.C. 154(b) by 291 days.

(21) Appl. No.: 18/682,927

(22) PCT Filed: Jul. 25, 2022

(86) PCT No.: PCT/DE2022/100536
§ 371 (c)(1),
(2) Date: Feb. 11, 2024

(87) PCT Pub. No.: WO2023/016601
PCT Pub. Date: Feb. 16, 2023

(65) Prior Publication Data

US 2024/0295471 A1 Sep. 5, 2024

(30) Foreign Application Priority Data

Aug. 13, 2021 (DE) ..................... 10 2021 121 165.4

(51) Int. Cl.
*G01N 1/14* (2006.01)
*G01N 33/24* (2006.01)
*G01N 1/10* (2006.01)

(52) U.S. Cl.
CPC ............. *G01N 1/14* (2013.01); *G01N 33/245* (2024.05); *G01N 33/246* (2013.01); *G01N 2001/1025* (2013.01); *G01N 2001/1418* (2013.01)

(58) Field of Classification Search
CPC ...... G01N 1/14; G01N 33/245; G01N 33/246; G01N 2001/1025; G01N 2001/1418; G01N 33/24
See application file for complete search history.

(56) References Cited

U.S. PATENT DOCUMENTS 10,564,122 B1 * 2/2020 Xu .................. G01N 27/44791
2021/0231548 A1 * 7/2021 Skaling .................. G01N 22/04

FOREIGN PATENT DOCUMENTS

DE 10121326 A1 2/2003
DE 102018206035 A1 10/2019
(Continued)

OTHER PUBLICATIONS

International Search Report issued on Oct. 31, 2022, in International Application No. PCT/DE2022/100536.

*Primary Examiner* — Xin Y Zhong
(74) *Attorney, Agent, or Firm* — Patent Central LLC; Stephan A. Pendorf

(57) ABSTRACT

A soil-water extraction device, with at least one matrix body (I), into which at least one channel (2) for receiving a soil-water sample is formed, a porous, hydrophilic ceramic (3), which likewise is introduced into the matrix body and which closes off the channel toward the soil side, flush with the matrix body (I), and a hose (4), which leads from the opposite side of the channel to a pump (5) driven by a motor driver (6), wherein: the motor driver (6) is controlled by means of a microcontroller (7); the microcontroller (7) is connected to at least one interface (8); and, by means of the interface (8), information about the moisture (9) is given to the microcontroller, said information being compared with stored target values (11). Also, a method for extracting soil water.

16 Claims, 4 Drawing Sheets

(56) References Cited

FOREIGN PATENT DOCUMENTS

| | | | |
|---|---|---|---|
| WO | 2012122050 | A2 | 9/2012 |
| WO | 2021074722 | A1 | 4/2021 |

* cited by examiner

FIG. 3
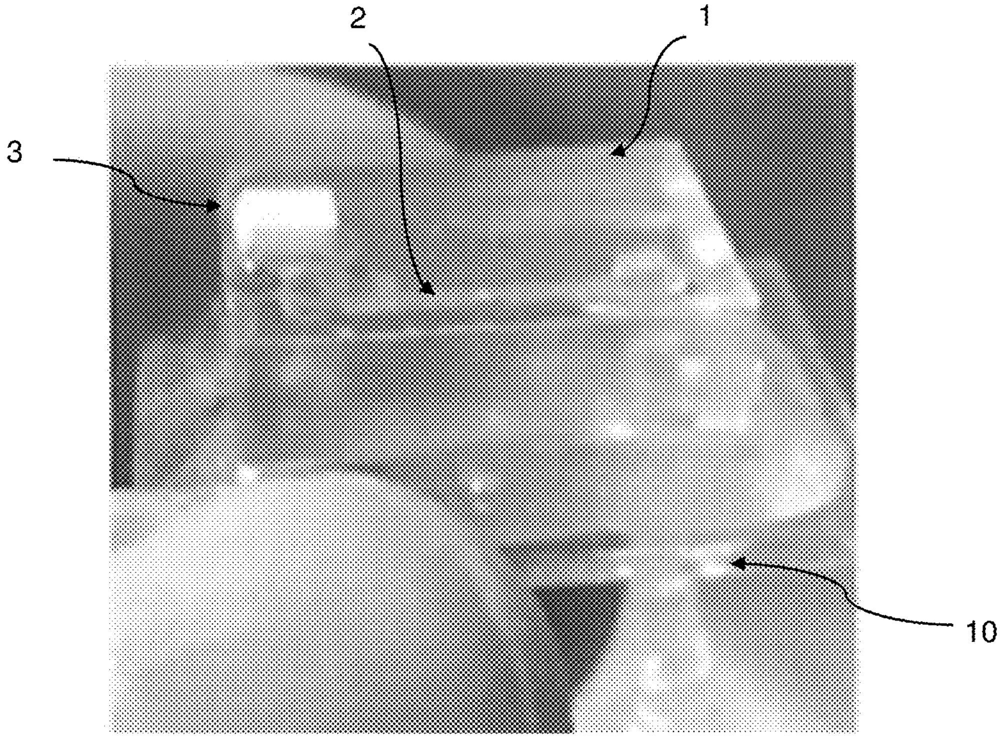
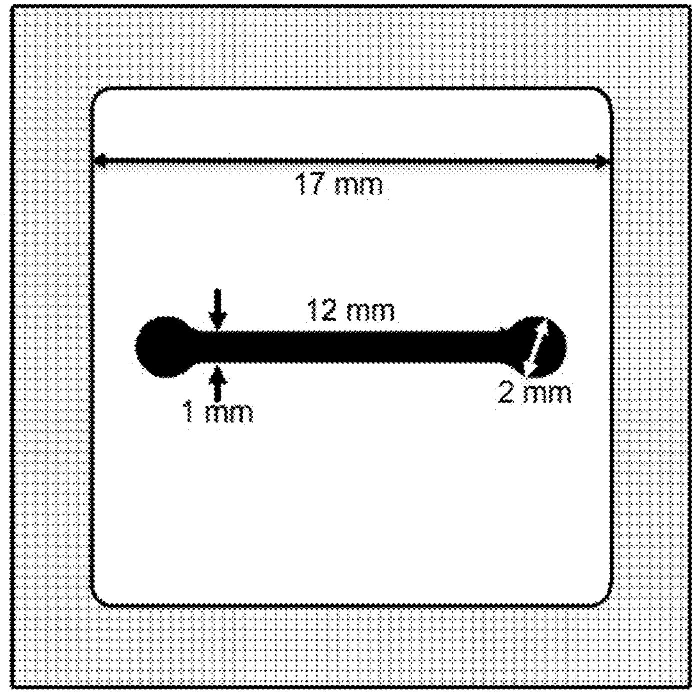
FIG. 4

DEVICE AND METHOD FOR EXTRACTING WATER FROM A SOIL SAMPLE

The invention relates to a device and a method for extracting seeping water to check the nutrient content in a soil sample.

In terms of effective and resource-saving agriculture, the accompanying testing of the soil for moisture, temperature, pH value and the content of nutrients, such as compounds of nitrogen (N), phosphorus (P), potassium (K) and iron (Fe), is of particular interest. The nutrients available to plants are found in the soil water, which is made up of the freely moving seepage water, the adhesive water held in the pores (pore water) and the stagnant water.

DIN 19746 (Deutsche Industrie Norm=German Industry Standard) describes a method for determining the mineral nitrogen in the form of nitrate (NO3−) and ammonium (NH4+) to determine the soil quality. The samples are taken on site, transported under refrigeration and first extracted in the laboratory in a field-moist state with a calcium chloride solution and then analyzed.

However, undisturbed soil samples in which the original position and structure of the soil is preserved are preferable for analyzing the water and nutrient content.

WO 2012/122050 claims a device for in situ analysis of the nutrient content of undisturbed soils, which consists of a “measuring unit” and a “sample-water collection unit”, whereby the latter is placed directly in the soil to be analyzed and remains there. The aim is to specifically extract the pore water and analyze it in a later step. In the course of seasonal cultivation of the soil to be examined, the device must be removed for planting and harvesting due to its size.

Furthermore, DE 10 2018 206 035 A1 discloses a suction cartridge for taking soil water samples, with a particularly hollow cylindrical housing that has an at least essentially closed and media-impermeable casing wall, whereby the housing has at least one opening that is closed by a liquid-permeable filter element, and a suction connection for generating a negative pressure in the housing, wherein it is provided that a collecting chamber is arranged in the housing, into which a fluid line connected to the opening leads, and that at least one sensor for determining a nutrient concentration, in particular ion concentration, of soil water located in the collecting chamber is arranged in the collecting chamber.

A measuring device for determining the physical properties of soil water is known from DE 101 21 326 A1, which has a housing with a semi-permeable membrane, a measuring section arranged inside the housing, which is in contact with the soil water via the semi-permeable membrane, and a controllable peristaltic pump connected to the measuring section, by means of which soil water can be pumped.

Furthermore, WO 2021/074 722 A1 discloses a system for collecting and chemically analyzing water samples taken from the soil in order to measure one or more analytes of interest, such as, for example, soil nutrient contents of agricultural crops. soil nutrient levels of agricultural interest to increase crop yield and quality in a use of the system, wherein the system includes a sample collection probe comprising a filter medium arranged to contact the soil when embedded therein and to receive a water sample from the soil, and operably coupled to a sample processing subsystem, thereby collectively forming a sample collection station, and the subsystem is configured to receive and analyze the water sample, wherein a programmable probe controller controls the operation of sample collection, sample processing and chemical analysis in situ.

For optimal monitoring of soil water quality, it is desirable to have continuous, fixed extraction of all soil water, uninterrupted by seasonal operations such as seeding, fertilizing, irrigating or harvesting.

In addition, it is also necessary to analyze the entire soil water in order to monitor the seepage water to protect the groundwater from the input of harmful substances and thus also to record the content of nutrients and pollutants in the seepage water.

In “Nutrient Sensing Using Chip Scale Electrophoresis and In Situ Soil Solution Extraction”, IEEE SENSORS JOURNAL, Vol. 17, No. 14, 2017, Xu et al. propose a miniaturized sensor unit for in situ soil analysis together with an extraction unit for soil water. The extraction unit has various tubes for supplying and removing the soil water and a filter in the form of a ceramic capillary tube with a filter membrane made of polyvinylpyrrolidone (PVP) and polyethersulfone (PES). Due to the high dead volume compared to the required sample volume, a pumping capacity is necessary which limits the autonomous battery operation of the entire device and thus the continuity of the measurement.

It is therefore the task of the invention to provide a device and a method that makes it possible to extract the soil water in situ, stationary, at short intervals over a longer period of time.

In one aspect, the task of the invention is solved by a soil water extraction device comprising at least one matrix body into which at least one channel for receiving a soil water sample is formed, and a porous, hydrophilic ceramic, which is likewise incorporated into the matrix body and which closes off the channel towards the soil side, flush with the matrix body, and a hose, which leads from the opposite side of the channel to a pump driven by a motor driver, wherein the motor driver is controlled by means of a microcontroller and the microcontroller is connected to at least one interface and by means of the interface information about the moisture is given to the microcontroller and is compared with stored target values.

Surprisingly, it was found that the combination of a porous, hydrophilic ceramic and a pump makes it possible to extract a sufficiently large sample volume, even with low power consumption of the pump.

In a particular embodiment, the porous, hydrophilic ceramic is made of aluminum oxide ($Al_2O_3$).

In a preferred embodiment, the power consumption due to the dimensioning of the pump drive is less than 1 W, preferably less than 500 mW, particularly preferably less than 400 mW.

In a further particular embodiment, the matrix body is attached to a substrate body.

In a further preferred embodiment, the microcontroller is connected to a further interface.

The matrix body can be made of glass, silicon or organic polymers. Preferred are organic polymers, which are particularly suitable for molding microfluidic structures, these are generally known to the skilled person or also from Christine Ruffert: “Technologies and materials for microfluidic systems” [DOI: 10.1007/978-3-662-56449-3_5]. The material for the matrix body is particularly preferably selected from the group consisting of polydimethylsiloxane (PDMS), polyimide (PI), polystyrene (PS), polypropylene (PP), polycarbonate (PC), cycloolefin copolymer (COC) and/or polyether ether ketone (PEEK).

The channel is produced according to methods known to the skilled person, for example from Christine Ruffert: “Technologies and materials for microfluidic systems”

[DOI: 10.1007/978-3-662-56449-3_5]. The width of the channel is between 1 μm and 5 mm, preferably between 10 μm and 3 mm.

The porous, hydrophilic ceramic is integrated into the matrix body and forms a planar surface with it. Integration into the matrix body can be achieved by punching and/or gluing. The average pore size of the porous hydrophilic ceramic is between 500 nm and 5 μm.

The volume of the pores in the total volume of the porous, hydrophilic ceramic is in the range between 20 and 60 percent by volume, preferably in the range between 30 and 50 percent by volume, particularly preferably in the range between 35 and 40 percent by volume.

The porous, hydrophilic ceramic can be selected from the group of carbides, nitrides, borides, silicides and oxides, preferably from the group of aluminum oxide, titanium dioxide, zirconium oxide, magnesium oxide and/or mixed forms of these oxides, particularly preferred is the porous, hydrophilic ceramic made of aluminum oxide ($Al_2O_3$).

Hoses—also for use in peristaltic pumps—are generally known to experts and can be purchased commercially.

The power consumption of the pump should be low so that long-lasting battery operation is possible. Pumps are generally known and commercially available. Suitable pumps with low power consumption are, for example, diaphragm pumps or peristaltic pumps. Particularly suitable diaphragm pumps are micro pumps from Mikrotechnik with a piezo diaphragm or mini diaphragm pumps, which are available from neoLab, for example. Suitable peristaltic pumps are available, for example, from Aquatech Co, Ltd. Peristaltic pumps usually have a stepper motor that is driven by a motor driver.

An example of a peristaltic pump is the model RP-QX1.2N from Aquatech Co., Ltd. here the power consumption is 0.36 W at 3 V.

Motor drivers are known to the specialist from electronics mail order companies and specialist catalogs such as RS-Components, Farnell or Digi-Key. Examples are TB6612FNG, L6506, TCA3727, DC motor driver: TB6612FNG.

Microcontrollers are single-chip computer systems that have a processor and peripheral functions. Examples here are a Raspberry Pi or an Arduino.

The microcontroller can be connected to an additional interface. It is possible to connect a computer or a display device via this additional interface.

The moisture information can be based on measured values that are determined directly on site. Such measuring devices are generally known to the skilled person, for example an SMT 100 from Truebner GmbH is suitable.

It is also possible to feed the moisture information from external data, such as weather stations, to the microcontroller via the interface.

Preferably, the data is transmitted to the microcontroller via the interface without contact and wirelessly and, if necessary, data is transmitted from the microcontroller via an interface to a display or a computer.

Target values are stored in the microcontroller, which are compared with the moisture information. If the soil moisture is sufficiently high and the preset minimum interval time is exceeded, the next extraction cycle for the soil solution analysis is initiated automatically.

The height of the substrate bodies should be small compared to their surface area. Platelet-shaped bodies made of glass, ceramic or organic polymers are suitable materials.

On the side of the channel opposite the hydrophilic ceramic, the substrate body has a hole for guiding and attaching the tube.

The matrix body can be attached to the substrate body by gluing, bonding, screwing or fusing.

In a further aspect, the invention is embodied by a method for extracting soil water comprising the following steps:

i. Transmitting information of the moisture to the microcontroller via an interface
ii. Processing the moisture information and comparing it with stored target values in the microcontroller
iii. Control of the motor driver of the pump by the microcontroller based on the result from step ii.
iv. Filling the channel and the hose with soil water using the ceramic and the pump operated by the motor driver.

FIG. 1 shows the schematic structure of the soil water extraction device according to the invention with a matrix body (1) in which at least one channel (2) for receiving a soil water sample is incorporated and a porous, hydrophilic ceramic (3) which is also incorporated in the matrix body and closes the channel flush with the matrix body on the soil side and a hose (4) which leads from the opposite side of the channel to a pump (5) which is driven by a motor driver (6), wherein the motor driver (6) is controlled via a microcontroller (7) and the microcontroller (7) is connected to at least one interface (8) and information about the moisture (9) is sent to the microcontroller via the interface (8) and compared with target values (11) stored there.

FIG. 3 shows a photograph of the matrix body with channel and glued-in ceramic attached to a substrate body measuring 2.5 cm×2.5 cm×0.1 cm.

FIG. 4 shows a sketch of the negative mold for molding the matrix body, the length of the channel is 12 mm, the volume of the channel is 12 μl.

Figure 5:
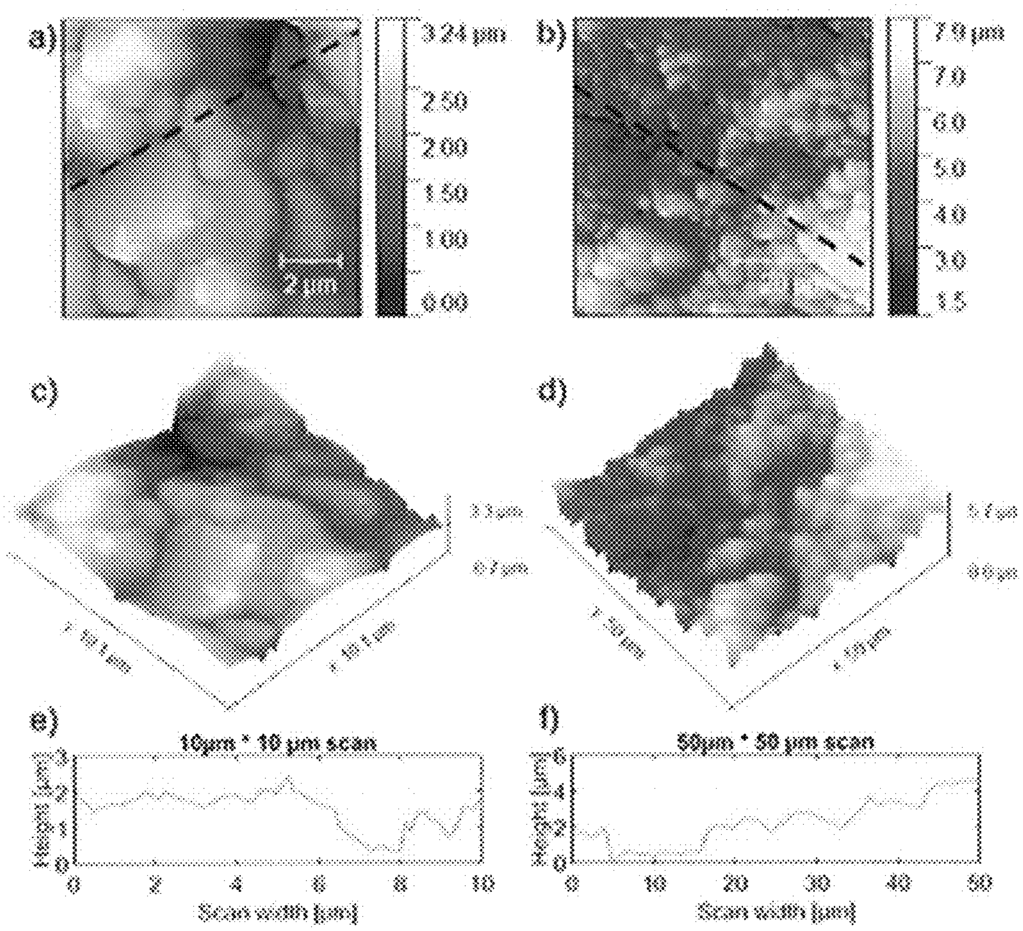

FIG. 5 shows the images of the hydrophilic ceramic used, taken using an atomic force microscope (AFM). Areas of 10 μm×10 μm (a, c) and 50 μm×50 μm (b and d) were examined. The height profiles (e and f) show a surface roughness between 2 μm and 4.2 μm.

Without limiting the overall scope of the invention, the application of the soil water extraction device according to the invention will be demonstrated in the following by way of example.

Exemplary Production of a Matrix Body with Channel and Ceramic

Based on the production drawing, the matrix body made of polydimethylsiloxane (PDMS) is molded using polytetrafluoroethylene (PTFE). For this purpose, the flowable PDMS prepolymer (SYLGARD® 184, Merck KGaA) is placed in the PTFE mold and cured at 90° C. within one hour. The cured fluidic body is then removed from the mold. A channel for the ceramic is then punched out so that it can be inserted flush into the fluidics and bonded.

The ceramic used is hydrophilic aluminum oxide (Al2O3). In this case, Keralpor 99, 99.5% Al2O3, Kerafol Keramische Folien GmbH & Co. KG, size 3 mm×2.5 mm×2 mm (length×width×height). The volume of the pores in the total volume of the porous, hydrophilic ceramic is between 36 and 38 percent by volume. The density of the hydrophilic ceramic is 2.56 $g/cm_3$ and the average pore size is 1 μm.

FIG. 5 shows the images of the hydrophilic ceramic used, taken using an atomic force microscope (AFM). Areas of 10 μm×10 μm (a, c) and 50 μm×50 μm (b and d) were examined. The height profiles (e and f) show a surface roughness between 2 μm and 4.2 μm.

The volume of the hydrophilic ceramic was determined by calculating the difference between the weight of the dehydrated hydrophilic ceramic (70.6 mg) and the water-saturated ceramic (84.3 mg) at 13.7 μl.

The matrix body is glued to a glass substrate body measuring 2.5 cm×2.5 cm×0.1 cm, which has a through hole on the side of the channel opposite the hydrophilic ceramic.

On the side of the channel opposite the hydrophilic ceramic, the substrate body has a hole for guiding and attaching the hose.

The hose is plugged into the substrate body and connected to a peristaltic pump (RP-Q1.2N, Aquatech Co., Ltd.).

A Raspberry Pi 4 and a motor driver for the peristaltic pump type TB6612 (Adafruit Industries) are used as the microcontroller. The moisture information is provided by a sensor of the type SMT100, Truebner GmbH.

Determination of the Soil Moisture Required for Extraction (Target Values):

The required soil moisture for three different types of soil (sand, garden soil and silt) is determined. The volume of the soil samples placed in the sealed container is 2500 $cm_3$.

Before starting the first measurement, the hydrophilic ceramic is moistened in order to have reproducible initial conditions. This is not necessary for continuous operation in the soil. The matrix body is then placed in the soil so that the ceramic is in direct contact with the soil. The sensor for recording the moisture in the soil is placed in the immediate vicinity of the matrix body.

In the experiment, the volume of extracted moisture in the channel is determined over time using a microscope. The soil moisture was varied by adding 100 ml of water at a time. The moisture was measured 15 minutes after adding the corresponding amount of water. The peristaltic pump was then operated for 30 minutes in each case.

Table 1 contains the measured moisture of the soil and the extracted volume for the different soils as a function of the added water.

An SMT 100 turbidity sensor was used for the experiments in Table 1. This has a specification range for the volumetric water content of the soil of 0 to 50% with an accuracy of +−3% with the factory calibration.

TABLE 1

Information of moisture and extracted volume for different soils

| | Sand | | Garden soil | | Silt | |
|---|---|---|---|---|---|---|
| Added water [ml] | measured moisture [Vol.-%] | Ex-tracted volume [ml] | Measured moisture [Vol.-%] | Ex-tracted volume [ml] | Measured moisture [Vol.-%] | Ex-tracted volume [ml] |
| 0 | 3 | 0 | 2 | 0 | 1 | 0 |
| 100 | 5 | 0 | 5 | 0 | 1 | 0 |
| 200 | 8 | 0.1 | 11 | 0.1 | 3 | 0 |
| 300 | 10 | 0.1 | 15 | 0.1 | 9 | 0 |
| 400 | 14 | 0.1 | 19 | 0.17 | 11 | 0 |
| 500 | 18 | 0.1 | 24 | 0.19 | 13 | 0.1 |
| 600 | 22 | 0.15 | — | — | 18 | 0.08 |
| 700 | 31 | 0.15 | — | — | 23 | 0.1 |
| 800 | — | — | — | — | 28 | 0.15 |
| 900 | — | — | — | — | 33 | 0.19 |

It is shown that extraction can start at a measured moisture of 8% by volume for sand, 11% by volume for garden soil and 13% by volume for silt.

Due to the different absorption capacity for water in the various soils, these values are achieved for garden soil and sand after the addition of 200 ml of water, whereas 500 ml must be added for silt in order to start extraction.

Depending on the required volume of the extracted sample and the nature of the soil, the target values can be rigidly set and stored in the microcontroller. This could be done by selecting the type of soil when it is added. Alternatively, a learning algorithm could be implemented that records the amount of water extracted at different pumping capacities and adjusts the target values based on this.

Further explanations on moisture are given below, which may be or are relevant for individual embodiments of the invention, but which are not necessarily limiting or must be limiting.

The moisture information is decisive for the invention in order to enable adaptive sampling, which is crucial for the low-energy operation of the sensor. Thus, if the soil is sufficiently moist, soil solution is extracted at a user-programmable minimum time interval. If the soil is drier than the minimum moisture value, the moisture information is evaluated regularly, e.g. every 5 minutes to every 6 hours. This can be transmitted to the sensor via weather data or read out with an associated soil moisture sensor.

The volumetric water content is the ratio between the water volume and the unit volume of the soil. The volumetric water content can be specified as a ratio, percentage or water depth per soil depth. Alternatively, a sensor that measures soil water tension can be used to determine soil moisture, e.g. from the reference Datta et al. (Datta et al., "Understanding Soil Water Content and Thresholds for Irrigation Management", Oklahoma Cooperative Extension Service, BAE-1537, June 2017). Accordingly, moisture information can be stored, transmitted and processed as volumetric water content or soil water tension.

The maximum volumetric water content is reached when all the pores (voids between the rigidly bound soil components) are filled with water. This saturation value varies between 30% in sandy soils and 60% in clay soils (reference Datta et al.). Above a certain threshold, water flows out of larger pores by gravity. This is the maximum soil moisture for irrigation and is also strongly dependent on the soil type (reference Datta et al.). Most agricultural soils reach the threshold one to three days after irrigation or a rain event. This means that the moisture information must be evaluated within this period in order to benefit from the increased soil moisture. The permanent wilting point determines the moisture above which plants can no longer extract water from the respective soil type. Soils should typically be kept above this moisture level so as not to put plants at risk. This value is therefore the relevant minimum soil moisture for the sensor system and is also dependent on the soil type.

Due to the differences in the saturation values and the permanent wilting point for different soil types, a rigidly fixed threshold value should not simply be used for operation.

Table 1 demonstrates this difference and provides guidelines for the choice of threshold value. Soil solution extraction should be activated for sandy soils from 8%+−3% volumetric water content, for silt from 13%+−3% volumetric water content and for mixed soils in between.

In the first method of adaptive sampling, this threshold value is stored in the microprocessor together with the soil information. As soon as this threshold is exceeded, the soil solution is extracted. If the soil moisture information is transmitted via the interface from other sensors, the threshold values are programmed in advance.

In the second method of adaptive sampling, the change in soil moisture is observed instead of the absolute value. After irrigation, the water content in the soil suddenly increases by more than 50% (reference Datta et al.). Here, the soil moisture is recorded with a sensor with a time resolution of greater than 30 min (i.e. shorter time intervals) and the soil solution extraction is activated as soon as a jump in soil moisture of more than 50% is observed.

TABLE OF FIGURES

Figure 1:
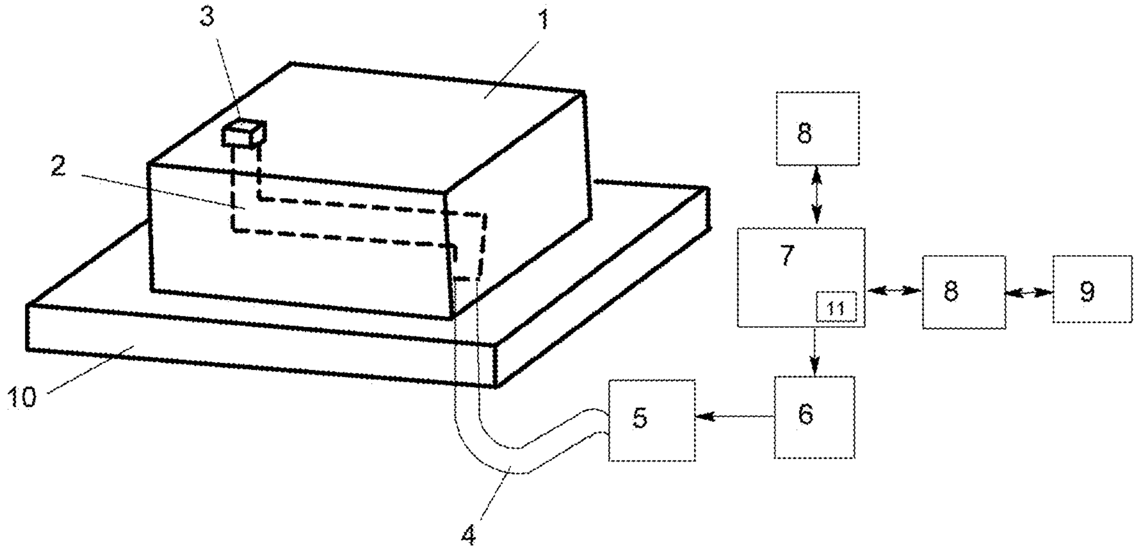
Figure 2:
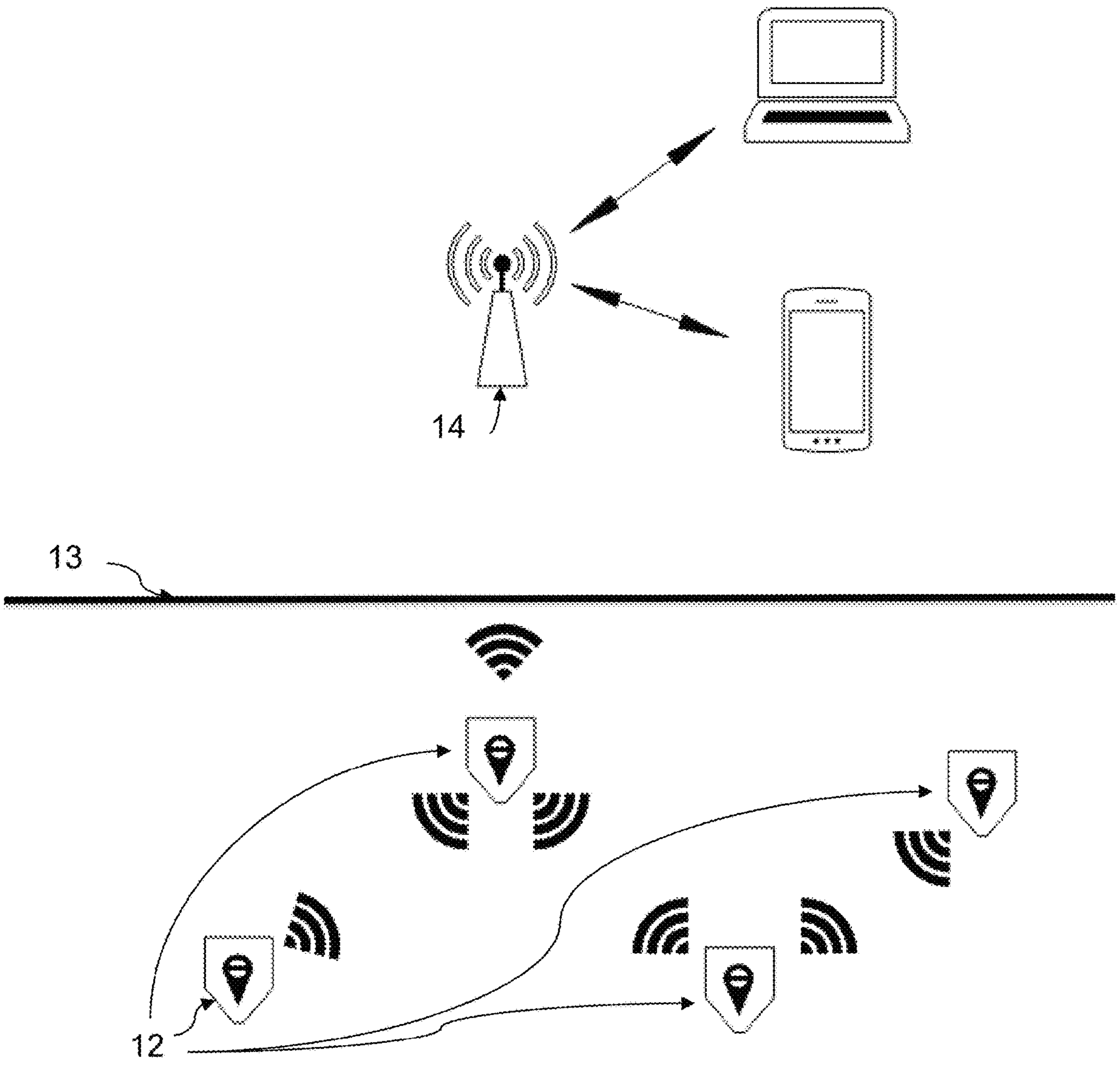
FIG. 2 shows a schematic representation of the application of the device according to the invention and the method in connection with the Internet of Underground Things (IoUT). The data is exchanged by radio via the gateway (14) between the sensor nodes (12) below the earth's surface (13) and the devices with the corresponding interface.

FIG. 1: Schematic representation of the soil water extraction device according to the invention FIG. 2: FIG. 2 shows a schematic representation of the application of the device according to the invention and the method in connection with the Internet of Underground Things (IoUT)

FIG. 3: Photograph of the matrix body with channel and glued-in ceramic attached to a substrate body measuring 2.5 cm×2.5 cm×0.1 cm FIG. 4: Sketch of the negative mold for the impression of the matrix body FIG. 5: AFM image of the hydrophilic ceramic made of $Al_2O_3$

LIST OF REFERENCE SYMBOLS

1 Matrix body
2 Channel
3 Ceramic
4 Hose
5 Pump
6 Motor driver
7 Microcontroller
8 Interface
9 Moisture information
10 Substrate body
11 Target values
12 Sensor node
13 Ground surface
14 Gateway

The invention claimed is:

1. A soil water extraction device comprising at least one matrix body (1) into which at least one channel (2) for receiving a soil water sample is incorporated, the channel (2) having an inlet and an outlet, a porous, hydrophilic ceramic (3) which is likewise incorporated into the matrix body and with an exposed surface closes off the channel towards the soil side, flush with the matrix body (1) and forming a planar surface with it, a hose (4) which leads from the outlet side of the channel (2) to a pump (5) which is driven by a motor driver (6), and a microcontroller (7), wherein the motor driver (6) is controlled by means of the microcontroller (7) and the microcontroller (7) is connected to at least one interface (8) and through the interface (8) information about the moisture (9) is given to the microcontroller during operation and are compared with stored target values (11), wherein the porous, hydrophilic ceramic is selected from the group consisting of carbides, nitrides, borides, silicides and oxides.

2. The soil water extraction device according to claim 1, wherein the porous, hydrophilic ceramic (3) is made of aluminum oxide ($Al_2O_3$).

3. The soil water extraction device according to claim 1, wherein the power consumption is less than 1 W due to the dimensioning of the drive of the pump (5).

4. The soil water extraction device according to claim 1, wherein the matrix body (1) is attached to a substrate body (10).

5. The soil water extraction device according to claim 1, wherein the microcontroller (7) is also connected to a further interface (8).

6. The soil water extraction device according to claim 1, wherein the material for the matrix body (1) is selected from the group consisting of polydimethylsiloxane (PDMS), polyimide (PI), polystyrene (PS), polypropylene (PP), polycarbonate (PC), cycloolefin copolymer (COC) and polyetheretherketone (PEEK).

7. The soil water extraction device according to claim 1, wherein the channel (2) has a width from 10 μm to 3 mm.

8. The soil water extraction device according to claim 1, wherein the average pore size of the porous hydrophilic ceramic (3) is from 500 nm to 5 μm.

9. The soil water extraction device according to claim 1, wherein the volume of the pores in the total volume of the porous hydrophilic ceramic (3) is in the range from 20 to 60 percent of the volume.

10. A method for extracting of soil water comprising the following steps:

placing the extraction device of claim 1 into soil, transmitting information of soil moisture (9) via an interface (8) to the microcontroller (7);

processing the information of the soil moisture (9) and comparison with stored target values (11) in the microcontroller (7);

actuating the motor driver (6) of the pump (5) by the microcontroller (7) on the basis of the basis of the result from the information processing and comparison step;

filling the channel and the hose with soil water by means of the ceramic and the pump (5) driven by the motor driver.

11. The soil water extraction device according to claim 1, wherein the power consumption is less than 500 mW due to the dimensioning of the drive of the pump (5).

12. The soil water extraction device according to claim 1, wherein the power consumption is less than 400 mW due to the dimensioning of the drive of the pump (5).

13. The soil water extraction device according to claim 1, wherein the volume of the pores in the total volume of the porous hydrophilic ceramic (3) is in the range from 30 to 50 percent of the volume.

14. The soil water extraction device according to claim 1, wherein the volume of the pores in the total volume of the porous hydrophilic ceramic (3) is in the range from 35 to 40 percent of the volume.

15. The soil water extraction device according to claim 1, wherein the material for the matrix body (1) is polydimethylsiloxane (PDMS).

16. A soil water extraction device comprising at least one matrix body (1) into which at least one channel (2) for receiving a soil water sample is incorporated, wherein the material for the matrix body (1) is selected from the group consisting of polydimethylsiloxane (PDMS), polyimide (PI), polystyrene (PS), polypropylene (PP), polycarbonate (PC), cycloolefin copolymer (COC) and polyetheretherketone (PEEK), a porous, hydrophilic ceramic (3) which is likewise incorporated into the matrix body and closes off the channel towards the soil side, flush with the matrix body (1), wherein the porous, hydrophilic ceramic is selected from the group consisting of aluminum oxide, titanium dioxide, zirconium oxide, magnesium oxide and/or mixed forms of these oxides, and a hose (4) which leads from the opposite side of the channel to a pump (5) which is driven by a motor driver (6), wherein the motor driver (6) is controlled by means of a microcontroller (7) and the microcontroller (7) is connected to at least one interface (8) and through the interface (8) information about the moisture (9) is given to the microcontroller during operation and are compared with stored target values (11).

* * * * *